United States Patent
Vines et al.

(10) Patent No.: US 9,700,585 B2
(45) Date of Patent: Jul. 11, 2017

(54) MULTIPOTENT PRENATAL STEM CELLS

(71) Applicant: NuTech Spine, Inc., Birmingham, AL (US)

(72) Inventors: Jeremy B. Vines, Birmingham, AL (US); Howard P. Walthall, Jr., Birmingham, AL (US)

(73) Assignee: NuTech Medical, Inc., Birmingham, AL (US)

( * ) Notice: Subject to any disclaimer, the term of this patent is extended or adjusted under 35 U.S.C. 154(b) by 320 days.

(21) Appl. No.: 14/038,274

(22) Filed: Sep. 26, 2013

(65) Prior Publication Data

US 2015/0216911 A1 Aug. 6, 2015

(51) Int. Cl.
*A61K 35/50* (2015.01)
*C12N 5/073* (2010.01)
*C12N 5/0775* (2010.01)

(52) U.S. Cl.
CPC .......... *A61K 35/50* (2013.01); *C12N 5/0605* (2013.01); *C12N 5/0668* (2013.01)

(58) Field of Classification Search
None
See application file for complete search history.

(56) References Cited

U.S. PATENT DOCUMENTS

2006/0222634 A1* 10/2006 Clarke et al. ............... 424/93.7
2007/0122903 A1* 5/2007 Rezania ............... C12N 5/0605
435/325

OTHER PUBLICATIONS

Bilic et al, Cell Transplantation, 2008, vol. 17, No. 8, pp. 955-968 (abstract only).*
Parolini et al, Stem Cells, 2008, vol. 26, pp. 300-311.*
Stadler et al. Cytotherapy, 2008, vol. 10. No. 7, pp. 743-752.*

* cited by examiner

*Primary Examiner* — Allison Fox
(74) *Attorney, Agent, or Firm* — C. Brandon Browning; Maynard, Cooper & Gale, PC

(57) ABSTRACT

The present invention relates to the isolation, propagation and use of prenatal stem cells. The cells are CD105 negative. In certain embodiments the cells are also SSEA-4 positive or negative, and c-kit negative. The cells may be isolated from a prenatal sample, for instance third trimester amniotic fluid or placental membrane. The cells may be combined with a biologically compatible solution or a biologically compatible matrix and utilized to treat a human subject. The invention also contemplated enriched populations of prenatal stem cells. The enriched cell population may be propagated in the appropriate culture medium and the resulting progeny cells utilized therapeutic applications.

12 Claims, 10 Drawing Sheets

MULTIPOTENT PRENATAL STEM CELLS

FIELD OF THE INVENTION

The present invention relates to the isolation, propagation and use of prenatal stem cells.

BACKGROUND OF THE INVENTION

Stem cells are found in all multicellular organisms and have the potential to develop into a multitude of cell types during early life and growth. Stem cells are characterized by their ability for self-renewal (i.e., maintaining their undifferentiated state during several rounds of cell division), and their potency (i.e., the ability to differentiate into specialized cell types). An adult stem cell is defined as an undifferentiated cell, found among differentiated cells in a tissue or organ that can renew itself and can differentiate to yield some or all of the major specialized cell types of the tissue or organ. The primary roles of adult stem cells in a living organism are to maintain and repair the tissue in which they are found. Scientists also use the term somatic stem cell instead of adult stem cell, where somatic refers to cells of the body (not the germ cells, sperm or eggs). Embryonic stem cells are defined by their origin (i.e., cells from the preimplantation-stage embryo).

Cell potency is a general term which describes the stem cell's ability to differentiate into different cell types. The more cell types a stem cell can differentiate into, the greater its potency. Totipotency is the ability of a single cell to divide and produce all of the differentiated cells in an organism, for example spores and zygotes. Totipotent cells are those with the greatest differentiation potential. Pluripotency refers to a stem cell that has the potential to differentiate into cells representative of any of the three germ layers: endoderm, mesoderm, or ectoderm (epidermal tissues and nervous system). Multipotency describes progenitor cells which have the gene activation potential to differentiate into multiple, but limited, cell types. Oligopotency is the ability of progenitor cells to differentiate into a few cell types. Finally, a unipotent cell is a stem cell has the capacity to differentiate into only one cell type.

In the realm of allogeneic stem cell therapies for regenerative applications, one of the most recognized and studied form of cells are mesenchymal stem cells (MSCs). These cells are generally multipotent and can be isolated from a variety of tissues, with the most common sources being adipose and bone marrow. MSCs, known for their immunosuppressive properties and ability to regenerate a variety of tissues, have been utilized for the treatment of pathologies such as graft versus host disease and in orthopedic tissue regenerative applications with relative success (Bobis, Jarocha et al. 2006; Bernardo and Fibbe 2012). However, as is the case with all adult derived stem cells, the efficacy of these cells depends on both the health and age of the donor from which the cells are isolated. In general, as people age, both the density and regenerative potential of their endogenous stem cell population declines (Caplan 1994; Zhou, Greenberger et al. 2008). Since MSCs utilized in allogeneic applications are generally harvested from cadaveric donors ranging anywhere from 20 to 85 years of age, variability in both MSC quality and efficacy is an unavoidable reality (Zaim, Karaman et al. 2012).

This is of even greater concern when cells are harvested for the purpose of allogeneic stem cell implantation, where the stem cell recipient's innate immunological responses can reduce the potential effectiveness of an already less than ideal population of stem cells (Liu, Wang et al. 2011). Furthermore, adult derived MSCs are limited in terms of their capability to differentiate into a wide range of cell types as they are typically limited to differentiation into cells of mesodermal lineage (Bobis, Jarocha et al. 2006).

Induced pluripotent stem cells (iPSCs) and embryonic stem cells are well-known stem cell sources that are commonly presented as a solution to rectify these problems. However, ethical and safety concerns, along with associated regulatory barriers, currently prevent both of these stem cell types from being recognized as an immediately available alternative to adult stem cell therapies (Okano, Nakamura et al. 2013).

In the search for improved cell sources for tissue regenerative therapies, amniotic fluid has drawn increasing interest, and studies involving cells derived from the amniotic fluid have grown in prevalence within the scientific literature. These cells are seen as an immediately available and attractive alternative to other commonly studied stem cells due to their enhanced differentiation potential relative to adult stem cells, enhanced immunosuppressive capabilities, safety relative to iPSCs, easy accessibility, and lack of ethical such as those associated with embryonic stem cells (Marcus and Woodbury 2008; Roelen, van der Mast et al. 2009; Murphy and Atala 2013). In regard to their safety and efficacy, multiple studies have found that these cells have been demonstrated to differentiate into cell types from all three germ layers; yet, they do not induce tumor formation when implanted in-vivo (In't Anker, Scherjon et al. 2003; Delo, De Coppi et al. 2006; De Coppi, Bartsch et al. 2007).

In most cases, amniotic fluid cells are isolated and characterized following amniocentesis within the second trimester. Unfortunately, amniocentesis is not a wholly viable means by which to obtain the amount of cells necessary for large-scale allogeneic cell therapies. This is due to the fact that the volume of fluid collected during amniocentesis is small, necessitating ex-vivo clonal expansion of cells and resulting in a greatly increased timetable for clinical adoption due to current regulatory barriers. In addition, the procedure itself carries various risks to both the mother and the fetus such as the induction of spontaneous abortion (Himes 1999), and its use in clinical practice may be reduced in favor of tests which allow extraction of fetal genetic material from the circulating maternal blood. In contrast, third trimester amniotic fluid can be collected in volumes of up to 400 ml and obtained during routine cesarean section without risk to either the mother or fetus. In this regard, the collection of amniotic fluid during elective cesarean section following full-term pregnancy is a more attractive alternative.

However, term amniotic fluid cells have received significantly less scientific study than cells derived from the fluid earlier in pregnancy. Furthermore, while it is known that the term amniotic fluid cell population is heterogeneous, little is known about the behaviour of particular subpopulations or appropriate methods of isolating and using such subpopulations.

What is needed in the art, therefore, are stem cells isolated from full-term amniotic fluid or prenatal membranes that represent a potentially improved population of cells for allogeneic therapies as compared to adult derived MSCs, and methods for isolating such cells.

SUMMARY OF THE INVENTION

In one embodiment, the present invention pertains to an isolated human prenatal stem cell that is CD105 negative.

The cell is at least multi-potent, and may also be pluripotent. In one embodiment, the cell is also c-kit negative. The cell may be sorted to be SSEA-4 positive or negative. The cell may be isolated from a prenatal sample, for instance a prenatal fluid like third trimester amniotic fluid. The cell may also be isolated from a prenatal membrane, for example placental membrane. The cell may be combined with a biologically compatible solution or a biologically compatible matrix and utilized to treat a human subject.

In an additional embodiment, the present invention provides an enriched population of isolated human prenatal stem cells that are essentially CD105 negative. In alternative embodiments, the enriched population is either essentially SSEA-4 positive or essentially SSEA-4 negative. In another embodiment, the enriched population is essentially c-kit negative. The population of cells may be isolated from a prenatal sample, for instance a prenatal fluid like third trimester amniotic fluid, recovered for example at elective c-section. The population may also be isolated from a prenatal membrane, for example placental membrane. The enriched population of cells may be combined with a biologically compatible solution or a biologically compatible matrix and utilized to treat a human subject.

In an additional aspect, the invention provides for a method of proliferating a population of cells enriched for human prenatal stem cells comprising selecting at least one cell from a human prenatal sample, wherein the cell is CD105 negative, introducing the selected cell to a culture medium; and proliferating the selected cell in the culture medium. In one aspect, the selecting of the CD105 negative cell involves the steps of incubating the cells from a human prenatal sample with a first antibody reactive to CD105 and selecting the cells from the human prenatal sample which do not react with the CD105 antibody. In a further aspect, the method comprises incubating the selected cells which do not react with the CD105 antibody with a second antibody reactive to SSEA-4 and selecting the cells which are either reactive or non-reactive with the SSEA-4 antibody. The selecting step of the above method may be accomplished by an immunoselection technique, for instance flow cytometry, fluorescence activated cell sorting or immune-magnetic selection. The cells may also be selected to be c-kit negative. The selection steps may be carried out in any order. The cells may be isolated from a prenatal sample, for instance a prenatal fluid like third trimester amniotic fluid, recovered for example during elective c-section. The cells may also be isolated from a prenatal membrane, for example placental membrane. The cells may be combined with a biologically compatible solution or a biologically compatible matrix and utilized to treat a human subject.

In an additional embodiment, the present invention discloses a method of harvesting human prenatal stem cells comprising providing a human prenatal sample, collecting cells from the sample and selecting CD105 negative cells from the sample. In a further aspect, the method comprises incubating the selected cells which do not react with a CD105 antibody with a second antibody reactive to SSEA-4 and selecting the cells which react or do not react with the SSEA-4 antibody. The selection steps may be carried out in any order. The cells may be isolated from a prenatal sample, for instance a prenatal fluid like third trimester amniotic fluid. The cells may also be isolated from a prenatal membrane, for example placental membrane. The cells may be combined with a biologically compatible solution or a biologically compatible matrix and utilized to treat a human subject. In an additional embodiment, the method further provides selecting c-kit negative cells.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

Figures 1A, 1B:
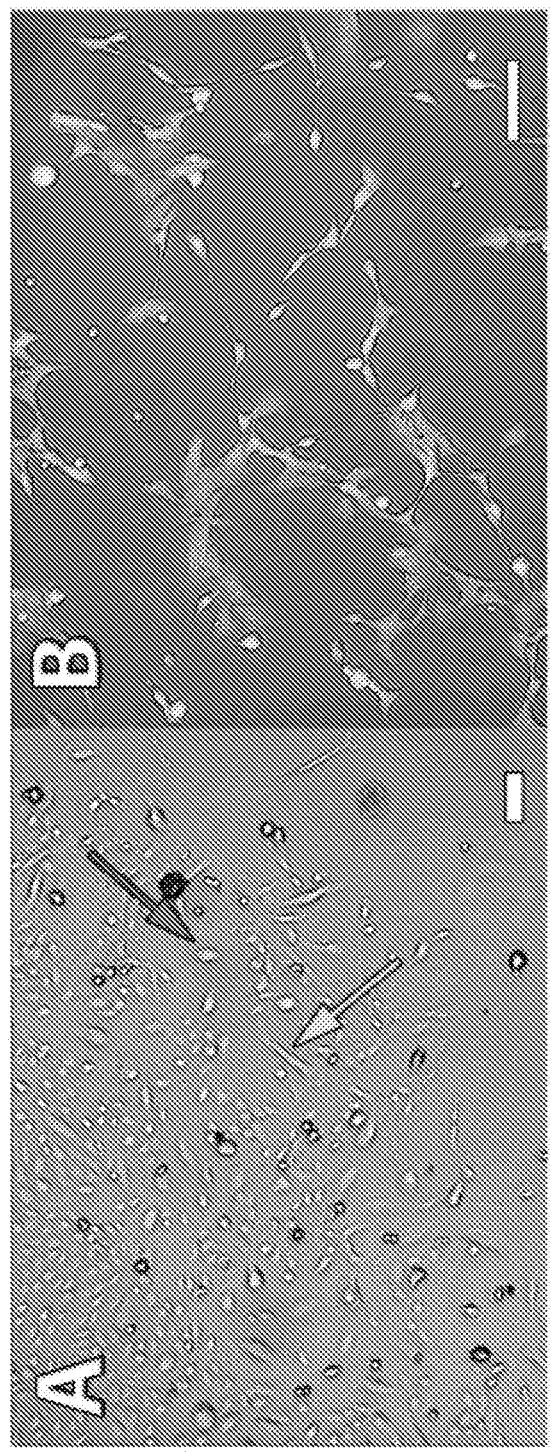
FIG. 1A is a photographic image of an amniotic fluid sample with a heterogeneous population of cells, at 4× magnification.
FIG. 1B is a photographic image of an amniotic fluid sample with a heterogeneous population of cells, at 10× magnification.
Figure 2A:
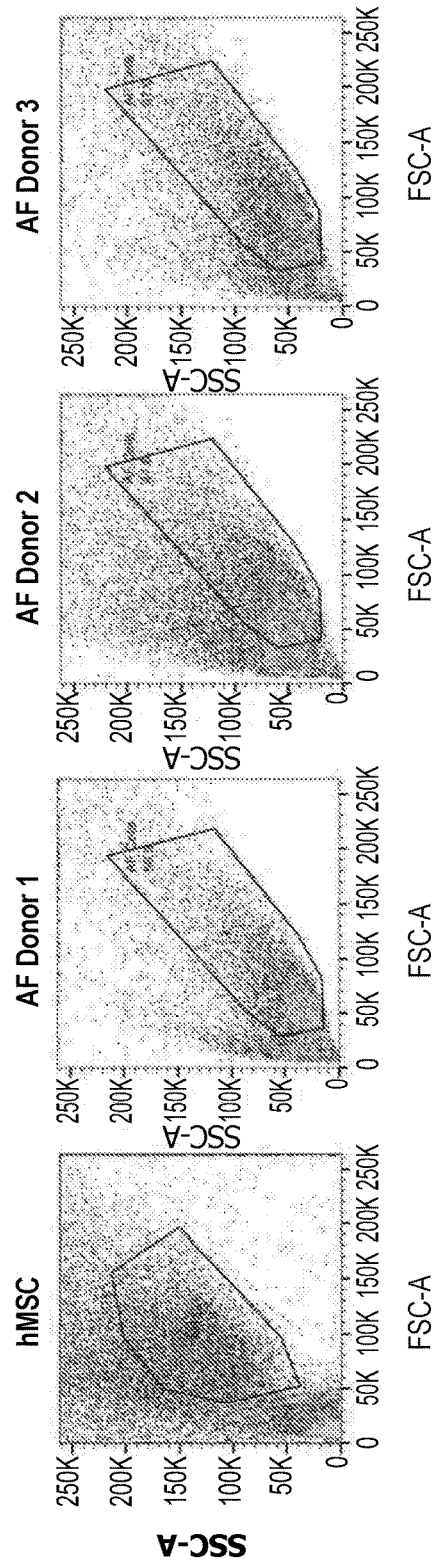
FIG. 2 is a graphical display of a FACS analysis of cell surface marker expression on bone marrow derived mesenchymal stem cells collected from three donors.
Figure 2B:
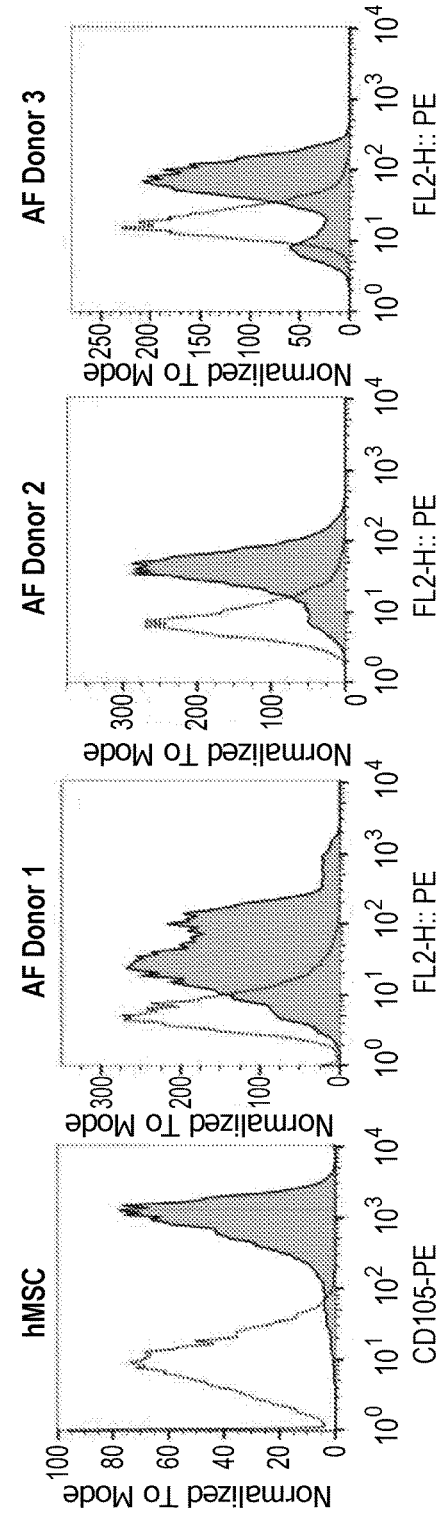
Figure 2C:
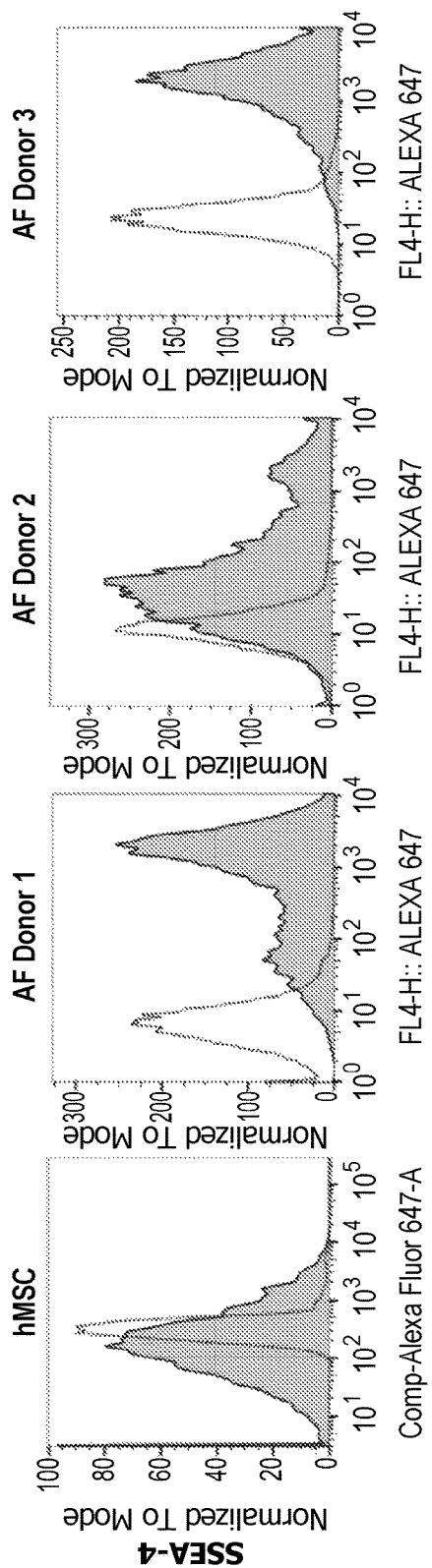
Figure 2D:
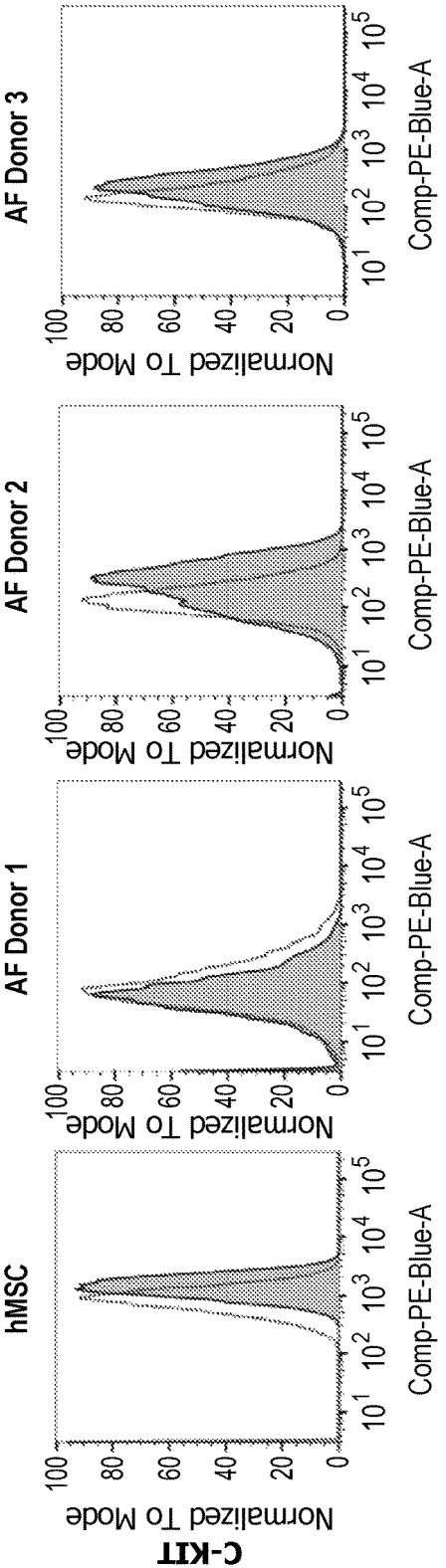
Figure 2E:
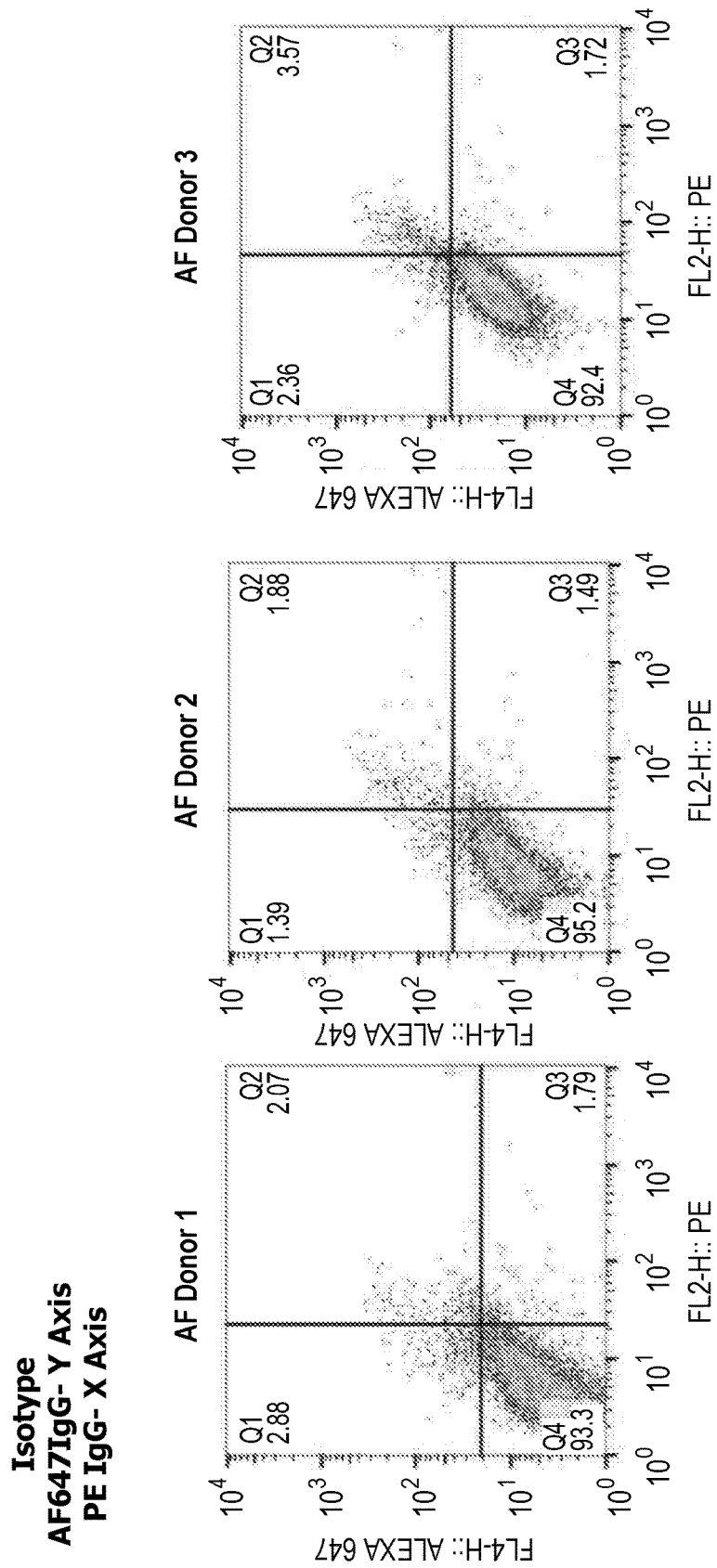
Figure 2F:
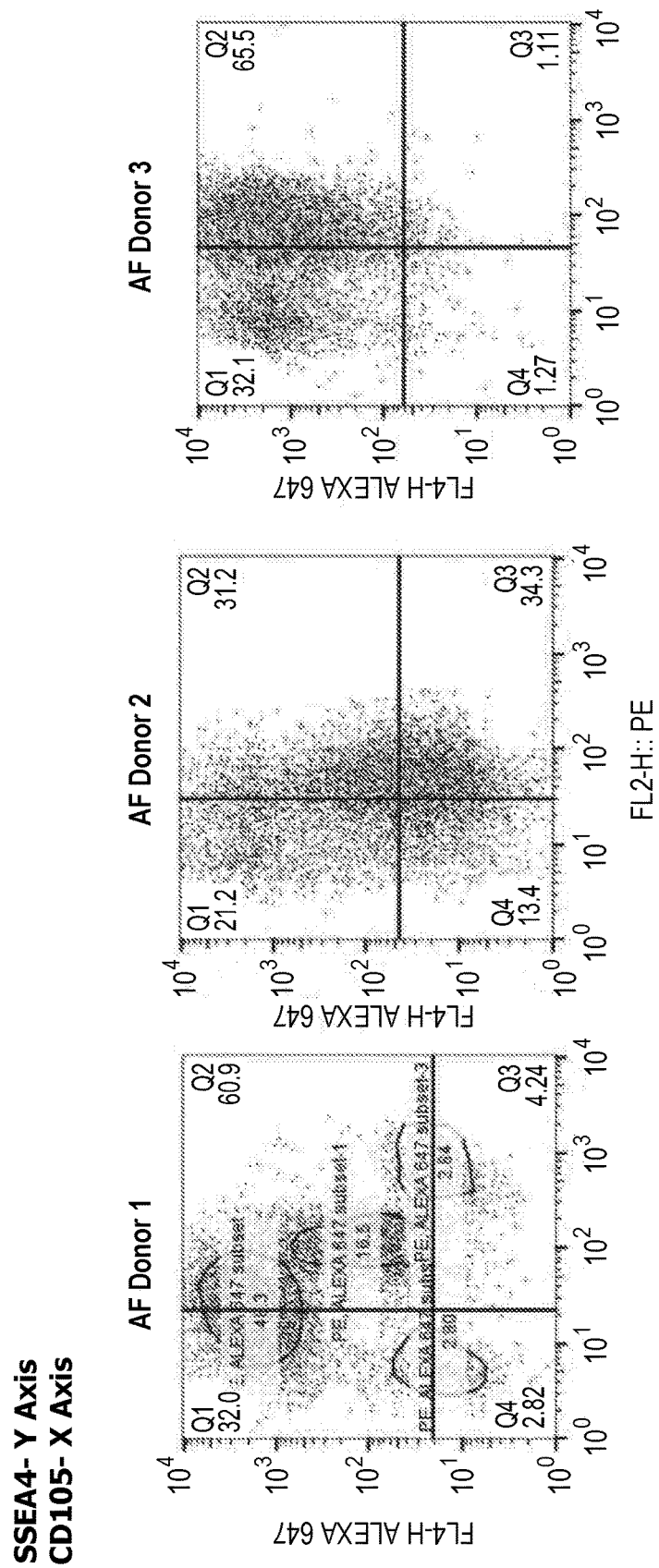

Before the present compositions, articles, devices, and/or methods are disclosed and described, it is to be understood that they are not limited to specific methods unless otherwise specified, or to particular reagents unless otherwise specified, and as such may vary. It is also to be understood that the terminology as used herein is used only for the purpose of describing particular embodiments and is not intended to be limiting.

This application references various publications. The disclosures of these publications, in their entireties, are hereby incorporated by reference into this application to describe more fully the state of the art to which this application pertains. The references disclosed are also individually and specifically incorporated herein by reference for material contained within them that is discussed in the sentence in which the reference is relied on.

The present disclosure describes prenatal stem cells isolated from prenatal fluids or tissue. Also disclosed are methods of propagating these stem cells as well as their therapeutic uses. In one embodiment, the prenatal stem cells are selected and propagated based upon the presence of certain markers, for example cell surface markers.

A "prenatal stem cell" herein refers to a cell originating from an embryonic or fetal mammalian organism and which is found in or isolated from a prenatal sample. The term "mammalian" as used herein, encompasses any mammal, for instance a human. A "prenatal sample" is defined herein as a prenatal fluid or tissue. The term "prenatal fluid" is defined as mammalian third trimester amniotic fluid. A "prenatal tissue" is the fetal component of a mammalian placental tissue, i.e., tissues originating predominantly from the fetus, for instance placental membranes. The prenatal stem cells of the present disclosure specifically exclude stem cells isolated or collected from an adult source, i.e., any maternal components or maternal tissue present in the mammalian placental membrane. A "stem cell" is a cell which has the potential to differentiate into multiple different cell types, and includes both multipotent and pluripotent cells.

In one embodiment, the prenatal stem cells are isolated from prenatal fluids (i.e., third trimester amniotic fluid) or tissues (i.e., placental membrane). Amniotic fluids such as third trimester amniotic fluid can be collected and obtained during routine cesarean section without risk to either the mother or fetus. Such collection techniques are known to one of skill in the art. The cells may then be separated from the surrounding fluid without significantly affecting their viability using centrifugation or other methods, also known in the art.

In an additional embodiment, the prenatal stem cells are isolated from a prenatal tissue, for instance placental membrane. The prenatal tissue may be collected via a tissue sampling technique. In one embodiment, a placental membrane sample may be collected by biopsy methods. Additionally, placental membranes may be collected from consenting donors shortly after birth. In particular, soon after the birth of a human infant via a Cesarean section delivery, the intact placenta is retrieved, and the placental membrane is dissected from the placenta. Afterwards, the placental membrane is cleaned of residual blood, placed in a bath of sterile solution, stored on ice and shipped for processing. Once received by the processor, the placental membrane is rinsed to remove any remaining blood clots, and if desired, rinsed further in an antibiotic rinse [Diaz-Prado S M, et al. *Cell Tissue Bank* 11, 183-195 (2010)].

The placental membrane may be processed to remove one or more particular layers of the membrane. The amnion and chorion (i.e., the fetal components) may be removed from the placental membrane by mechanical means well-known to those skilled in the art. The amnion and chorion may be removed, for example, by carefully peeling the chorion from the remainder of the placental membrane using blunt dissection [Jin C Z, et al. *Tiss Eng* 13, 693-702 (2007)]. The cells may then be released from the membrane without significantly affecting their viability using collagenase or other treatments, as known in the art.

In an additional embodiment, the cells extracted from a prenatal sample are then sorted based upon the expression of makers. The markers may be detected by various immunological methods, for instance immunohistochemistry or enzyme-linked immune assays (ELISA). The cells isolated from the prenatal fluid or tissue sample may be selected for the presence of a particular marker, for instance surface markers, intracellular markers or secreted proteins. These cells may be sorted by cell sorting techniques utilizing antibodies binding to the marker.

Some markers are unique to fetal or prenatal stem cells. For instance, stage specific embryonic antigens (SSEAs) are a group of glycolipid carbohydrate epitopes. One such antigen, SSEA-4, is expressed upon the surface of human teratocarcinoma stem cells (EC), human embryonic germ cells (EG) and human embryonic stem cells (ES). Expression of SSEA-4 is down regulated following differentiation of human EC cells. In contrast, the differentiation of murine EC and ES cells may be accompanied by an increase in SSEA-4 expression.

CD105 (commonly referred to as Endoglin END, FLJ41744, HHT1, ORW and ORW1) is a type I membrane glycoprotein located on cell surfaces and is part of the TGF beta receptor complex. CD105 plays a crucial role in angiogenesis. c-Kit (also known as CD117 or tyrosine-protein kinase Kit) is a protein that in humans is encoded by the KIT gene. Multiple transcript variants encoding different isoforms have been found for this gene.

Disclosed herein are prenatal stem cells which do not express CD105 antigens. Such cells are selected (i.e., isolated from CD105 expressing cells) using CD105 antibodies. In some embodiments of the invention, the prenatal stem cells are also SSEA-4 positive or negative and are therefore reactive or non-reactive to SSEA-4 antibodies. In an additional embodiment, the prenatal stem cells are c-kit negative. These cells may also be non-reactive to c-kit antibodies. Antibodies reactive to SSEA-4, CD105 and c-kit are commercially available and known in the art.

In certain embodiments, the marker antibodies (i.e, the SSEA-4, CD105 and c-kit antibodies) may be conjugated with certain molecules, such as a label, to assist in the identification and separation of the desired prenatal stem cells. Such labels may include, for example, fluorescein (FITC), phycoerythrin (PE), Cy5PE, Cy7PE, Texas Red (TR), allophycocyanin (APC), Cy5, Cy7APC, Cascade Blue, biotin, avidin and streptavidin. The antibodies are generally added to a cell sample in a concentration sufficient to allow for binding to the cell or cell population of interest, as will be known to one of skill in the art. The antibody and cells are incubated so that complexes are formed.

The use of such cell surface antigens provides a means of selecting for particular prenatal stem cell populations. For example, the prenatal stem cells may be selected for by flow cytometry utilizing a conjugated CD105 antibody (i.e., fluorescence activated cell sorting (FACS)). Magnetic selection using antibody-conjugated magnetic particles or beads is also possible. Other immune-selection methods, for instance those utilizing solid phase chromatography, are also contemplated. One of skill in the art will appreciate that many techniques may be employed for the immune-separation of the desired prenatal stem cells.

In an additional embodiment, the CD105 negative prenatal stem cells are selected for based upon the expression (or non-expression) of other cell surface markers, such as SSEA-4 and c-kit. Utilizing methods similar to those described above for CD105, the prenatal stem cells may be selected based upon being negative for, as an example, SSEA-4 and c-kit. These selection techniques may also employ, for example, FACS, antibody-conjugated magnetic particles or solid phase chromatography. These markers may be used to isolate the desired prenatal stem cells from a mixed cell population.

In an additional embodiment, the present invention comprises a cell population enriched for prenatal stem cells not bearing the CD105 marker. The term "enriched population" refers to a population where CD105 negative prenatal stem cells will comprise 30% or more of the cell composition, preferably 50% or more of the cell composition, or more preferably 75% or more of the cell composition when compared to the non-desired prenatal stem cells. Such a cell population is characterized as CD105 negative and may be identified and characterized based on the expression of this marker. As detailed above, a SSEA-4 positive population may be isolated from a prenatal source (i.e., prenatal fluid or prenatal membrane) by immune-isolation methods such as cell sorting, magnetic particle sorting or solid phase chromatography utilizing SSEA-4 antibodies. Such methods are well known to one of skill in the art.

Additionally, the a population of prenatal stem cells may be substantially free of cells which specifically bind and/or are reactive to the CD105 antibody; i.e., such cells do not express the CD105 marker. As used herein, the term "substantially free of", as used for example in reference to the number of prenatal stem cells which are CD105 positive, refers to a number of cells in amounts ranging between 0 to 15% of the total cell population.

Optionally, the above described CD105-enriched prenatal stem cell population is essentially c-kit negative, i.e., does not express the c-kit marker. As used herein, the term "substantially c-kit negative", refers to a number of c-kit positive cells in amounts ranging between 0 to 15% of the total cell population.

In one embodiment, the prenatal stem cells are first selected for the SSEA-4 surface marker by incubation with a labeled SSEA-4 antibody and sorting by an immune-selection technique, as described previously. Those cells which are SSEA-4 positive are then incubated with labeled CD105 antibodies and selected as described previously. Those cells which do not react with the CD105 antibody (i.e., are essentially CD105 negative) optionally may then be incubated with labeled c-kit antibodies and sorted accordingly for those cells which do not react with the c-kit antibody (i.e., are essentially c-kit negative). The resulting cells or enriched cell population is then characterized as SSEA-4 positive and essentially CD105 and c-kit negative. A specifically defined cell population may be selected, propagated and harvested utilizing the above described method.

In alternate embodiments, selection may be done in an alternate order. Thus, for example, cells which do not react with a CD105 antibody may first be selected, followed by selection for cells which do or do not express the SSEA-4 surface marker.

The enriched prenatal stem cell population, selected for as described above, may be harvested or collected in an appropriate cell propagation medium, such as Hank's Basic Salt Solution (HBSS), RPMI, Dulbecco's Modified Eagle Medium (DMEM), Iscove's modified Dulbecco's medium (IMDM) or Dulbecco's phosphate buffered saline (dPBS). This medium may be supplemented, for instance with fetal calf serum (FCS), bovine serum albumin (BSA), human serum albumin (HSA), recombinant human albumin (RHA), HEPES buffer, Insulin, Transferrin, Selenium, etc. The cell medium allows for the growth of the cells under controlled conditions. Additionally, in order to maintain their endogenous state and promote healthy culture, the cells may be propagated on a substrate consisting of either natural extracellular matrix proteins or synthetic derivatives such as Collagen, Fibronectin, Laminin or a synthetic peptide coating. The enriched cell populations may then be propagated to expand their numbers. The term "propagated", as defined herein, refers to increasing the number of viable cells in a particular culture, typically by growing the cells through one or more cell cycles.

The viability and proliferation of the cells may be measured utilizing techniques well known in the art. Cell viability may be measured by staining the cells with various dyes. Tools for measuring cell proliferation include probes for analyzing the average DNA content and cellular metabolism in a population, as well as single-cell indicators of DNA synthesis and cell cycle—specific proteins. In some embodiments, the cells are proliferated through one to ten or more passages, and the number of cells assessed at predetermined time points to assess the rapidity of cell proliferation and of population growth.

In one embodiment, the prenatal stem cells or cell population may be propagated in the presence of a reagent that suppresses differentiation. Such reagents are known in the art and include leukemia inhibitory factor, stem cell factor and certain metal ions. In an additional embodiment, reagents may be added to the prenatal stem cells or cell population to induce differentiation, for example $Ca^+$, hydrocortisone, keratinocyte growth factor and collagen.

The propagated prenatal stem cells of the invention may secrete various hormones, enzymes, growth factors, etc., that may be useful for the treatment of various diseases or conditions. The cell supernatant derived from the cultures of the enriched prenatal stem cell population may be harvested or collected in order to isolate and purify these various molecules.

The presently described prenatal stem cells and stem cell populations, or secretions therefrom, may be used to treat individuals suffering from various diseases and conditions, particularly those conditions caused by a loss of or damage to poorly-regenerating portions of the body or a lack of a secreted composition, such as a hormone, growth factor or enzyme. Such diseases or conditions may include immune deficiencies, neurological disorders, inflammatory conditions, ischemic conditions or injuries to any portion of the body. Treated portions of the body may include bone, cartilage, tendon, muscle, skin, cardiac muscle, and nerves. In one embodiment, the prenatal stem cells and stem cell populations may be used to regenerate or reconstruct tissue for wound or soft tissue repair. Such treatments may involve the combination of the described stem cells, cell populations, or secretions therefrom with a biologically compatible solution or a biologically compatible matrix.

As used herein, the term "treat" refers to any type of treatment which imparts a benefit to an individual in need thereof. "Treat" may also refer to the alleviation of one or more symptoms. A "subject", as used herein, is any mammalian subject and may include a patient or individual in need of therapy or treatment.

A "biologically compatible solution" refers to a synthetic or natural solution which may be placed in intimate contact with living tissue without damage to such tissue. A biologically compatible solution has compositions and properties similar to solutions made by a living organism and thus will not harm the organism or cause adverse reactions within the organism. A preparation including a biologically compatible solution combined with the prenatal stem cells, stem cell populations, or secretions of the present invention may be used for the parenteral administration into a subject in order to treat a specific condition. Such administration may be done intravenously, intramuscularly, subcutaneously or through implantation.

A "biologically compatible matrix" refers to a synthetic or natural solid or semi-solid material used to replace, replicate or supplement tissues normally found in the mammalian body. Such matrices may include, for example, synthetic bone, cartilage or tissue. The matrix may also comprise ground substances in which biological materials are attached to or imbedded, or a mesh-like network which may cover, protect or support organs or wounds. In one embodiment, a preparation comprising the prenatal stem cells, stem cell populations or secretions of the present invention and a biologically compatible matrix may be implanted into a subject to support cell growth, tissue regeneration, wound healing, etc.

The prenatal stem cells and stem cell populations described above as well as the supernatant collected from the culture of such cells and cell populations, may serve to enhance regeneration and healing of wounds and provide hormones, growth factors or enzymes not present in the body.

EXAMPLE

The following example is presented to provide those of ordinary skill in the art with a complete disclosure and a description of how the compounds, compositions, and methods described and claimed herein are made and evaluated. The following examples are intended to be purely exemplary and are not intended to limit the scope of what the inventors regard as their invention. There are numerous variations and combinations of conditions, e.g., component concentrations, desired solvents, solvent mixtures, temperatures, pressures and other reaction ranges and conditions that can be used to optimize the product from the described process. Only reasonable and routine experimentation will be required to optimize such process conditions. As will be understood by those familiar with the art, the present invention may be embodied in other specific forms without departing from the spirit or essential characteristics thereof.

Initial Culture and Morphological Observation

Amniotic fluid from three consenting donors was collected via vacuum aspiration during elective cesarean section into a surgical vacuum canister. The fluid was then shipped to the laboratory on ice for next day delivery. Following receipt, the fluid was aliquoted to 50 CC tubes, centrifuged, and re-suspended in cell culture media. The cell suspensions were then introduced to T-75 flasks and placed into a humidifying incubator (37° C., 5% $CO_2$, 95% Humidity) for long-term expansion.

After a few days of culture, there was an emergence of multiple colony forming unit fibroblasts (CFU-Fs). Referring to FIG. 1A, the morphology of cells within these CFU-Fs appeared mixed, with some cells exhibiting a spindle shaped morphology characteristic of fibroblasts (arrow 10) and MSCs and others exhibiting a more rounded morphology characteristic of epithelial cells (arrow 12) (image taken at 4× magnification). Scale bar 14 represents 100 μm. FIG. 1B represents a magnified image of a CFU-F predominated by spindle-shaped amniotic fluid cells (image taken at 10× magnification). Scale bar 146 represents 100 μm. This observation is in line with the findings of others in which it was determined that amniotic fluid is a heterogeneous mixture containing different cell types (Antonucci, Iezzi et al. 2009; Zhang, Geng et al. 2010; Roubelakis, Trohatou et al. 2012).

Fluorescence Activated Cell Sorting (FACS) Analysis

Following initial expansion, the cellular composition of the amniotic fluid donor populations was characterized via fluorescence activated cell sorting (FACS) analysis for an array of cell surface markers traditionally characteristic of MSCs (CD90, CD105, CD44) and pluripotent stem cells (SSEA-4). Cells were also tested for the presence of CD117 (c-kit) and an MHC Class II immunological antigen (HLA-DR) as well as a typical immunological and endothelial cell-type marker (CD31). Bone marrow derived MSCs were also characterized to serve as a comparison and control group. The antibody for each cell surface marker was compared to the expression of its respective isotype antibody in order to determine positive expression. The results of the cell surface marker expression for each marker are illustrated in Table 1. The results of the FACS analysis are illustrated in FIG. 2.

Cells were first gated to separate viable populations from cellular debris via forward and side scatter. Cells were then assessed for CD31 expression to test for the presence of endothelial, blood, and immunological-type cell populations. CD31, also known as PECAM-1, is typically found on the surface of endothelial cells, platelets, macrophages, T/NK Cells, lymphocytes, megakaryocytes, osteoclasts, and neutrophils. For each amniotic fluid donor, as well as for the MSCs, the vast majority of each cell population was negative for CD31, reflecting the lack of hematopoietic and endothelial cell-type contamination. In order to assess the immunogenicity of MSCs and amniotic fluid cells, the expression of HLA-DR was tested. In all cell types, HLA-DR was not expressed, highlighting the lack of immunogenicity in all cell types.

Cells were further assessed with mesenchymal stem cell panels for CD90, CD105, and CD44. All cell types and amniotic fluid batches were strongly CD90 positive (FIG. 2). CD44, a cell-surface glycoprotein involved in cell-cell interactions, cell adhesion, and migration is said to be expressed on both MSCs and amniotic fluid derived stem cells (Roubelakis, Pappa et al. 2007). As expected, CD44 was strongly expressed in all amniotic fluid donor cells as well as MSCs, corresponding to results found in other studies.

CD105 was strongly expressed in MSCs and differentially expressed among the three fluid donors, with a portion of the total population for each donor testing positive and negative. This profile is likely a reflection of the fact that the amniotic fluid contains a heterogeneous population of cells. Furthermore, CD105 expression is reported to vary in amniotic fluid cell cultures based on which cell subtype predominates the culture (Tsai, Lee et al. 2004; De Coppi, Bartsch et al. 2007; Zhang). In adult cell populations, the presence of CD105 is considered to be a telltale marker of a therapeutically effective MSC (Dominici, LeBlanc et al. 2006).

CD117 (also known as C-Kit) is a mast/stem cell growth factor receptor that is known to be present on certain types of mesenchymal stem cells and has been found to be positive on subset populations of amniotic fluid cells. Once again, like CD105, c-kit is differentially expressed depending on the amniotic fluid subtype dominating the culture (Zhang, Geng et al. 2010). This fact was also reflected in the present results, where AF donor 1 was c-kit negative and AF donors 2 and 3 expressed low levels. C-kit positivity also appeared to positively correlate with CD105 positivity. C-kit positive amniotic fluid derived cells have been demonstrated to have a higher affinity to differentiate into different lineages than c-kit negative cells (Arnhold, Gluer et al. 2011; Bai, Wang et al. 2012). This fact was elucidated by Bai et. al, who found that both c-kit+ and c-kit– cells are able to differentiate into adipogenic and osteogenic lineages but noted that c-kit+ cells had enhanced myocardial differentiation relative to their c-kit– counterparts. A number of researchers have suggested the use of c-kit positivity as a marker for selection

TABLE 1

Results of the cell surface marker expression.

| Donor | Cell Surface Marker Expression | | | | | | |
|---|---|---|---|---|---|---|---|
| | CD31 | CD90 | CD105 | CD44 | CD117 (c-kit) | SSEA-4 | HLA-DR |
| AF Donor 1 | Negative | Positive | Mixed | Positive | Negative | Positive | Negative |
| AF Donor 2 | Negative | Positive | Mixed | Positive | Low | Mixed | Negative |
| AF Donor 3 | Negative | Positive | Mixed | Positive | Low | Positive | Negative |
| MSC | Negative | Positive | Positive | Positive | Low | Negative | Negative | of a therapeutically beneficial amniotic fluid cell population (De Coppi, Bartsch et al 2007; Pozzobon, Piccoli et al. 2013).

In order to determine whether cells were likely to express markers related to pluripotency, cells were assessed for the presence of Stage-specific embryonic antigen 4 (SSEA-4). SSEA-4 is a surface molecule typically found in embryonic cells. It is commonly associated with early-stage pluripotent cells such as embryonic stem cells and induced pluripotent stem cells. In contrast to MSCs, all of the amniotic fluid derived cells expressed SSEA-4 to varying degrees, with AF donors 1 and 3 exhibiting strong expression and AF donor 2 demonstrating a mixed expression. This finding was unexpected as prior researchers have reported that amniotic fluid stem cells are generally SSEA-4 positive. (Kim, Lee et al. 2007; Roubelakis, Pappa et al. 2007; You, Tong et al. 2009; Zhang, Geng et al. 2010; Arnhold, Gluer et al. 2011). The reasons for this finding are unknown, but may relate to either donor variability, cell subtype differences, or differences in culture conditions, including the number of population doublings.

Cellular Growth Profile Analysis

To characterize fluid cell growth rates relative to MSCs, cells from all three donors were seeded on 48 well tissue culture plates (BD Biosciences, San Jose, Calif.) at a density of ~10,000 cells/cm$^2$ in replicates of six for each donor and allowed to incubate for 7 days. Cells were then collected at days 1, 4, and 7 and quantified utilizing a Picogreen dsDNA assay (Invitrogen, Carlsbad, Calif.). To determine the amount of cells present in each sample, cells were determined to have 7.88×10-6 µg of DNA per cell. In order to compare cell morphology and density over time between the three amniotic fluid donors and MSCs, cells were stained with Phalloidin (Invitrogen, Carlsbad, Calif.) and 4',6-diamidino-2-phenylindole (DAPI) (Invitrogen, Carlsbad, Calif.) and imaged under fluorescence with a Nikon TE2000-S microscope (Nikon Instruments, Melville, N.Y.).

Figure 3:
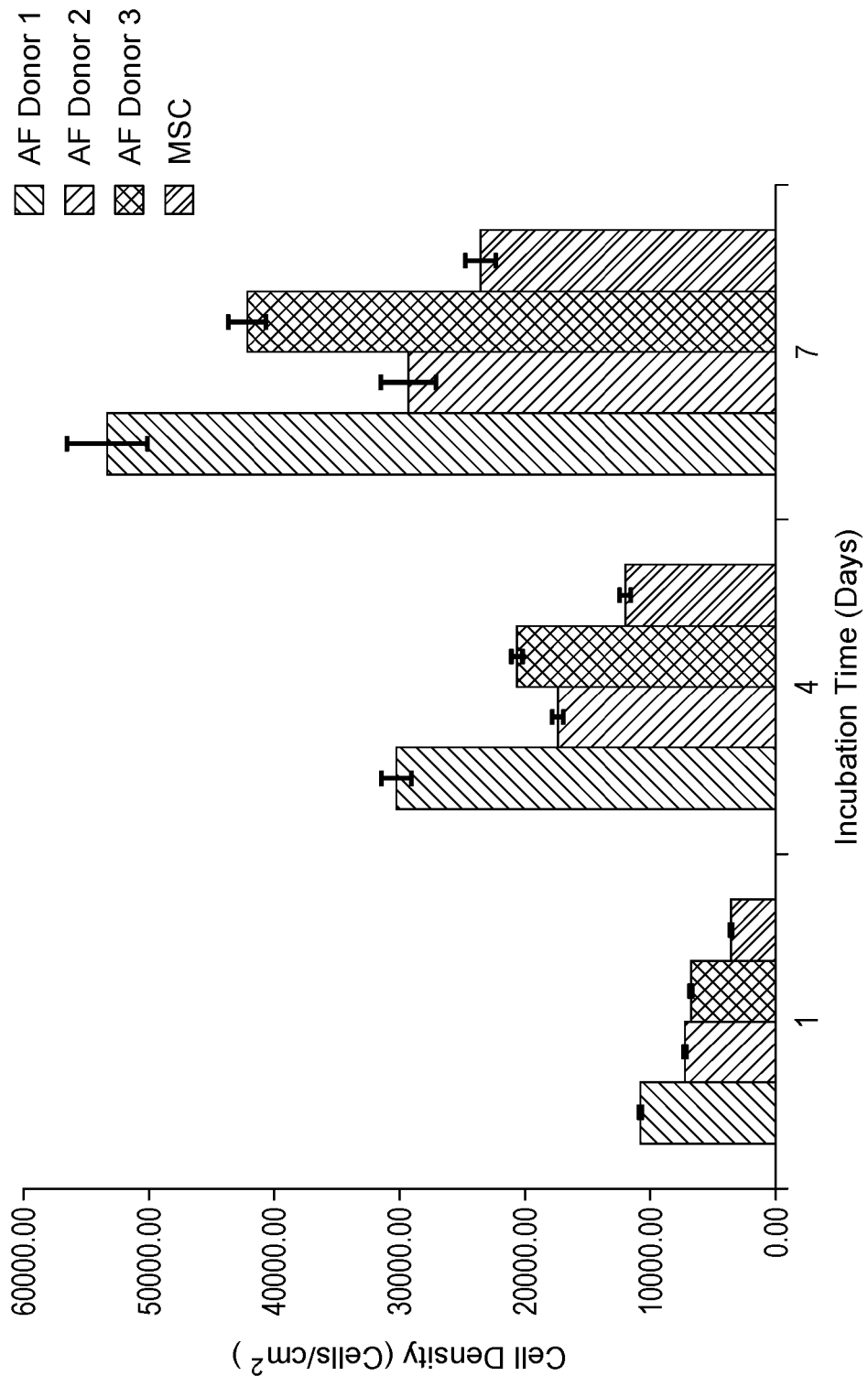
FIG. 3 is graphical display of a measurement of amniotic cell proliferation over time.
Figure 4:
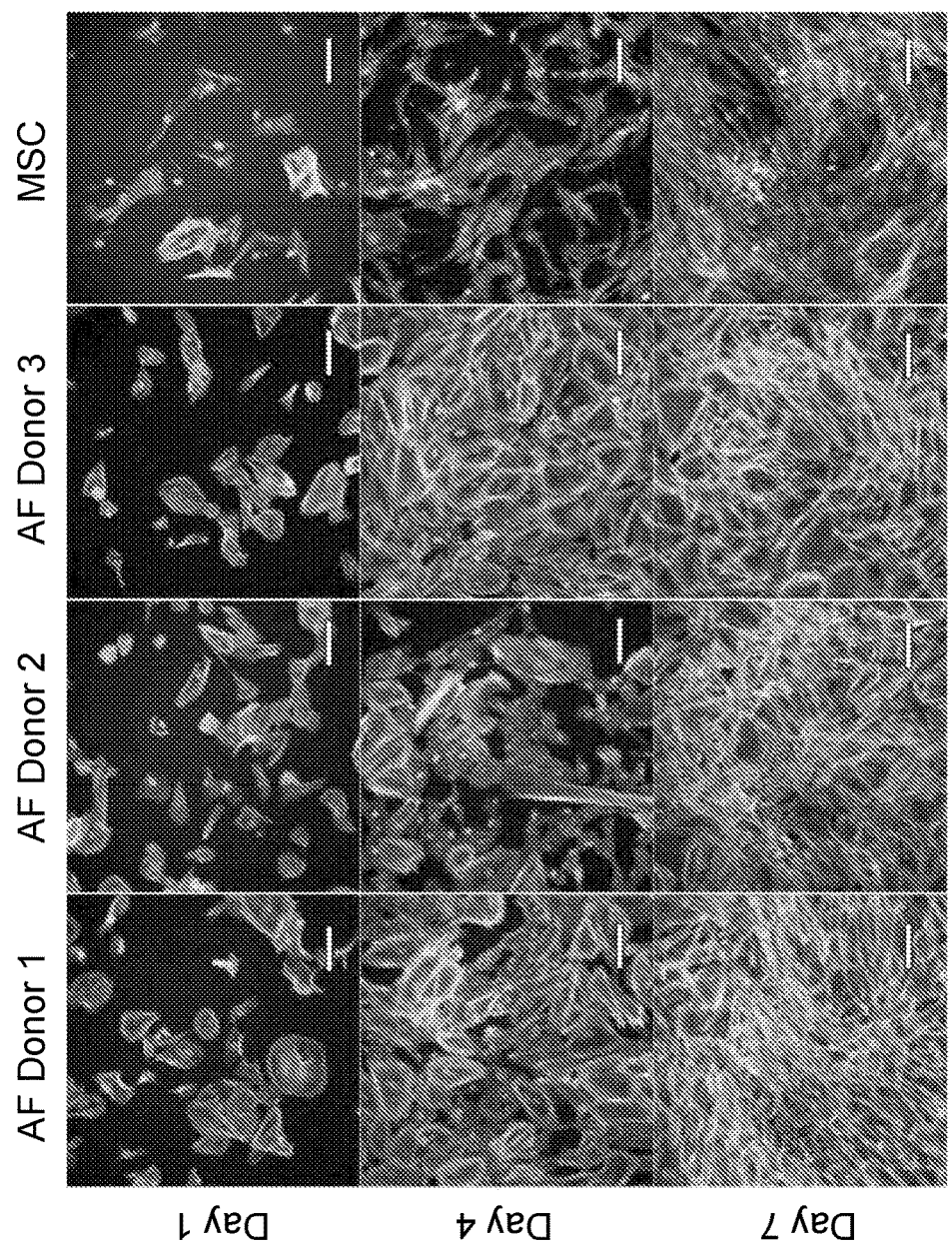
FIG. 4 is a photographic morphology image of individual fluid donor cell populations in comparison to MSCs over 7 days.

Referring now to FIG. 3, the observed results indicate that the amniotic fluid derived cells grew faster than the MSCs, demonstrating statistically significant differences. However, while the cellular growth rate of all amniotic fluid donors was greater than that of MSCs, AF donor 2, which exhibited the lowest level of SSEA 4 positivity but the highest level of c-kit positivity, exhibited lower growth rates when compared to AF donors 1 and 3. Referring to FIG. 4, these results are collaborated by morphological imaging of the individual fluid donor cell populations in comparison to MSCs over 7 days. Here, the cells were cultured for up to seven days after seeding at equal densities. The cells were fixed and stained with Phalloidin and DAPI at days 1, 4 and 7 of culture (image taken at 20× magnification). Scale bar 20 represents 100 µm.

Osteogenic Differentiation

Figure 5:
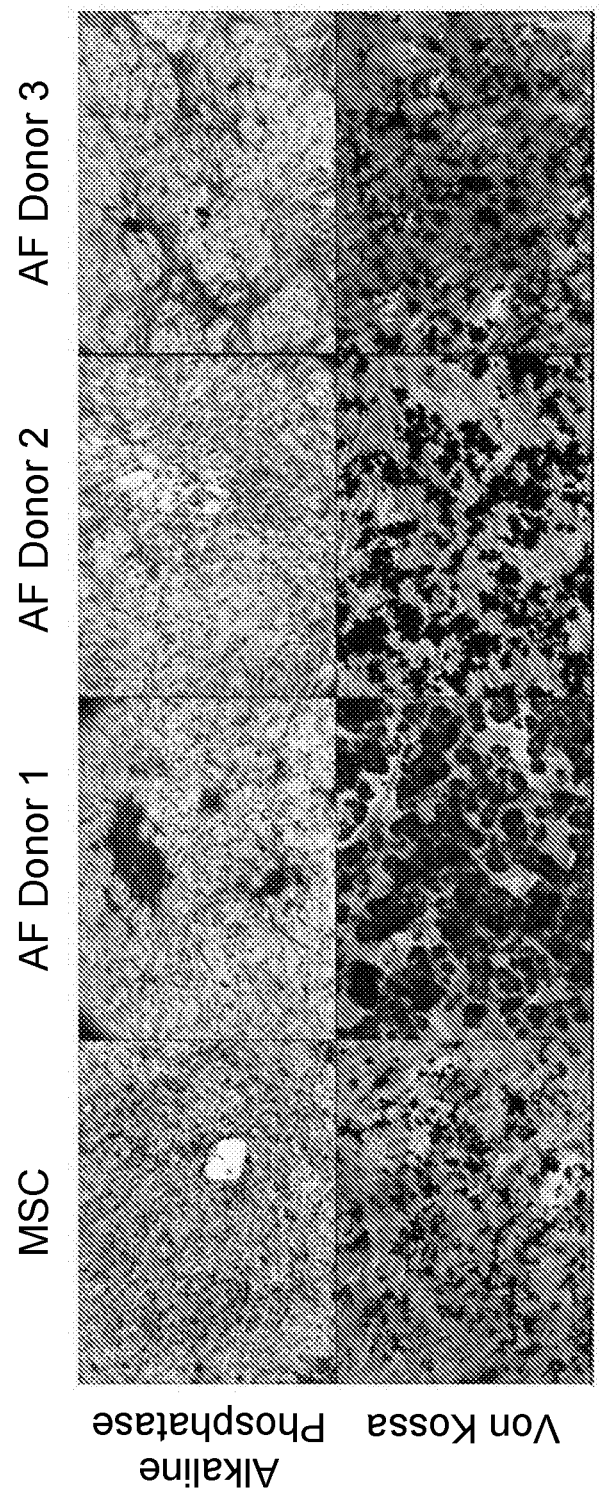
FIG. 5 is a photographic image of the osteogenic differentiation of amniotic fluid derived cells.

In order to confirm the capability of the amniotic fluid cells to undergo osteogenic differentiation, cells were cultured in osteogenic supplement medium containing 100 nM dexamethasone, 0.05 mg/mL L-abscorbic acid, and 10 mM β-glycerol phosphate for up to 28 days. Cells were then tested for Alkaline Phosphatase (ALP) activity by staining with p-nitro blue tetrazolium chloride (NBT) and 5-bromo-4-chloro-3-indolyl phosphate (BCIP) (Invitrogen, Carlsbad, Calif.) and for calcium deposition by staining with a Von Kossa mineralization kit (American Mastertech, Lodi, Calif.) following 14 and 28 days of culture, respectively. The results are illustrated in FIG. 5. The density of ALP at day 14 appeared slightly greater for the MSC cells than that of the amniotic fluid donor cells. However, observed mineralization at day 28 was much greater for the amniotic fluid derived cells relative to the MSCs. This peculiar phenomenon has also been observed in a similar study by Peister et al, in which spindle shaped amniotic fluid cells demonstrated lower levels of initial ALP activity, yet, greatly increased levels of mineral deposition over time (Peister, Woodruff et al. 2011).

FACS Sorting

In order to determine the proliferation rate of various amniotic fluid derived cell populations sorted by fluorescence activated cell sorting (FACS), cell populations from two of the three donors were seeded at 10,000 cells/cm$^2$ in replicates of six in 48 well tissue culture plates and assessed for cellularity over days 1, 4, and 7. A total of 8 populations derived from two different amniotic fluid donors were assessed.

The populations were (Donor Number, Surface Marker Expression Profile):

Donor 2, CD105−SSEA4+
Donor 2, CD105−SSEA4−
Donor 2, CD105+SSEA4+
Donor 2, CD105+SSEA4−
Donor 3, CD105−SSEA4+
Donor 3, CD105−SSEA4−
Donor 3, CD105+SSEA4+
Donor 3, CD105+SSEA4−

Each population was defined by its individual cell surface antigen co-expression of CD105 and SSEA4 via FACS sorting.

Cells were cultured in 48 well tissue culture plates and assessed for cell number at days 1, 4, and 7. At each time point, cells were collected in 0.25% trypsin and subjected to a freeze-thaw cycle. Following this, total DNA content was measured using a Picogreen dsDNA kit. Total cell number was then calculated by dividing total DNA content by average DNA content per cell.

Average growth rates of each cell type were calculated using the formula:

$$\frac{\frac{1}{\text{Day1}} + \frac{1}{\text{Day4}}}{(\text{Day1} - \text{Day4}) \; (\text{Day4} - \text{Day7})}{2}$$

Where Day1, Day 4, and Day 7 refer to cell number at days 1, 4, and 7.

Figure 6:
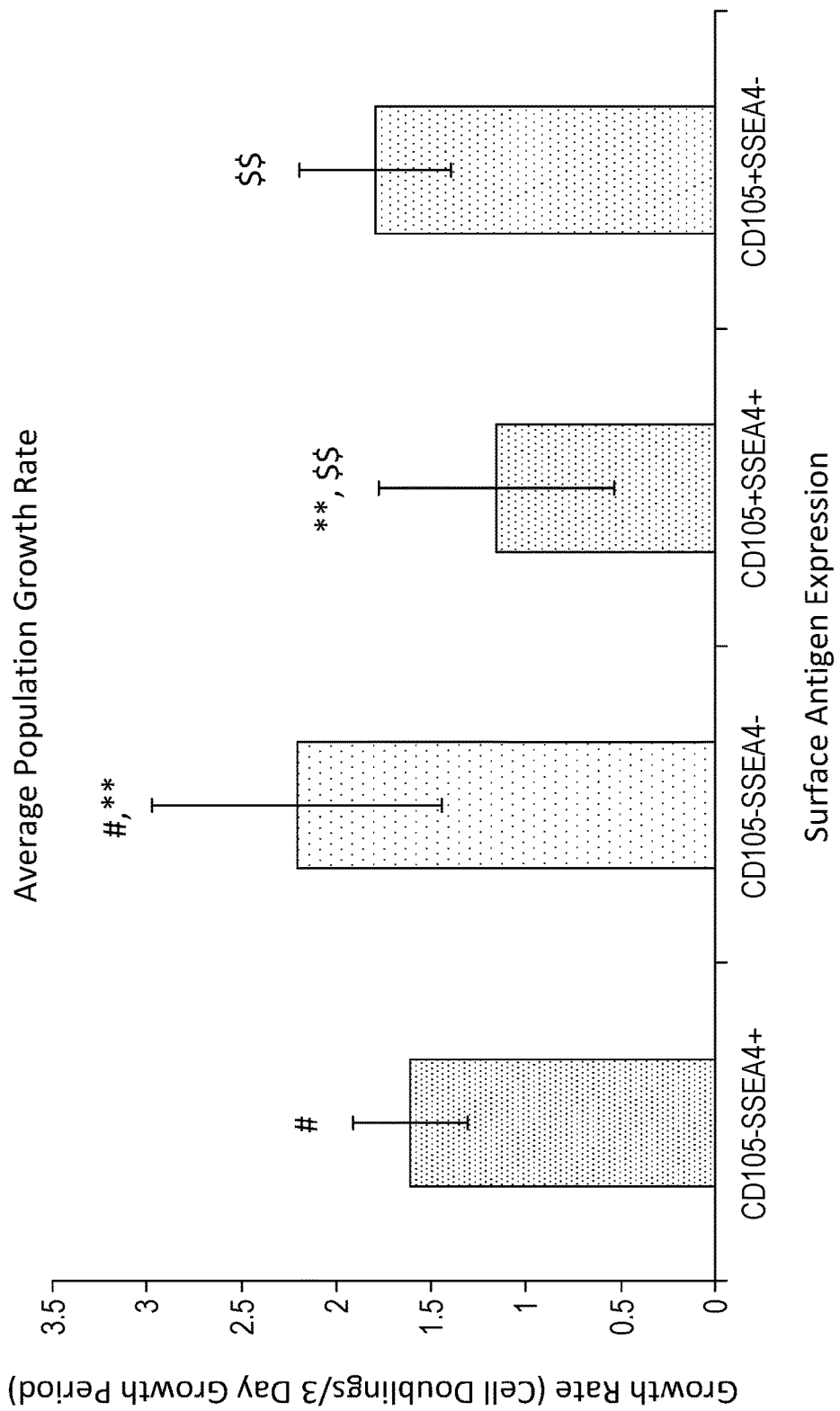
FIG. 6 is a graphical display of a measurement of amniotic cell proliferation in different sorted populations over time.
Figure 7:
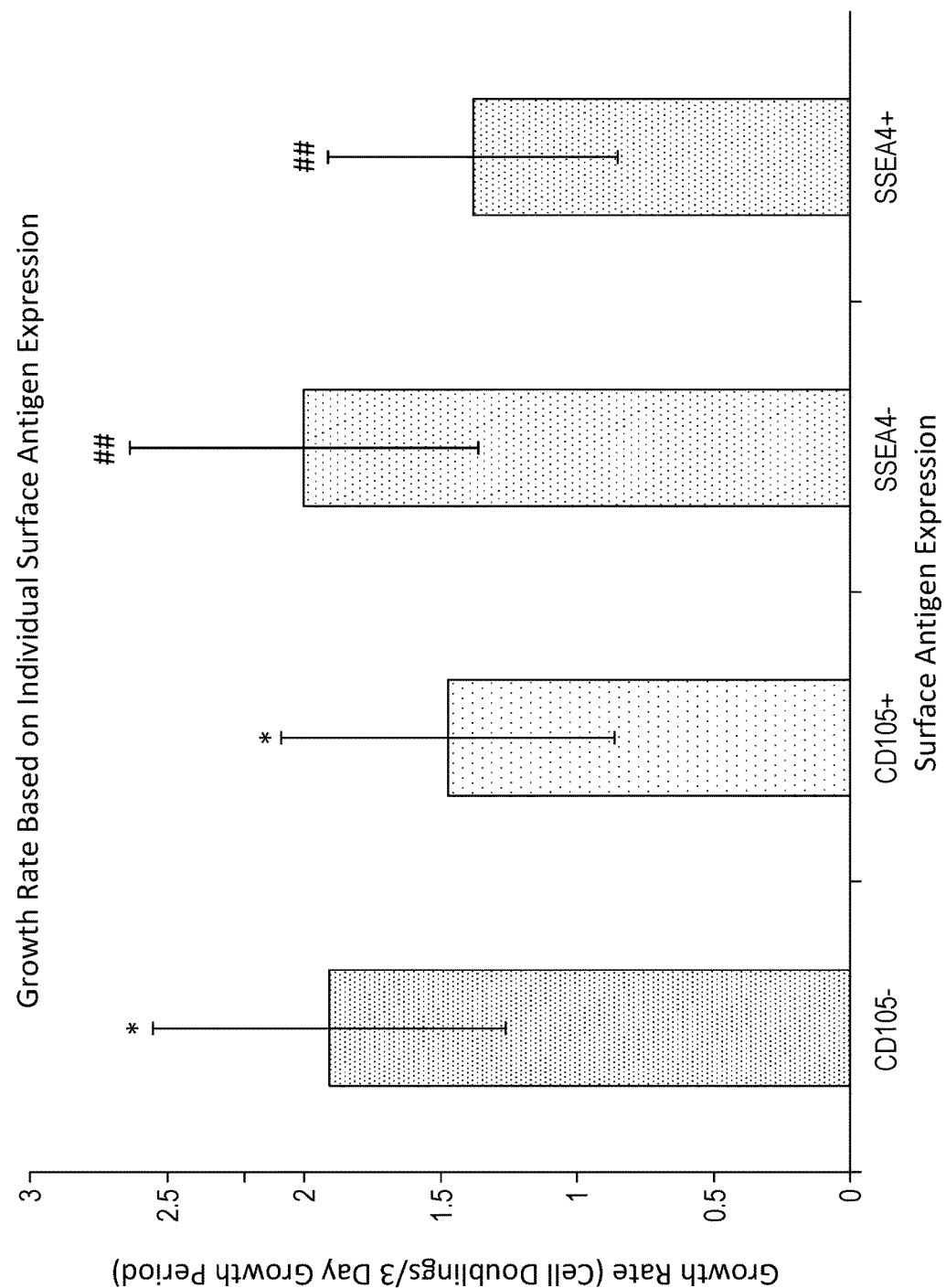
FIG. 7 is a graphical display of a measurement of amniotic cell proliferation based on surface marker expression over time.

Following this, growth rates among the various sorted cell populations were grouped and assessed based on their cell surface antigen expression and tested for the presence of statistically significant differences as reflected in FIGS. 6 and 7. #=p<0.05, **,$$=p<0.01. Error bars represent Standard Deviation Based on the data, the observed trends were as follows: In terms of proliferation rate CD105−SSEA4−>(CD105−SSEA4+~CD105+SSEA4−)>CD105+SSEA4+. The data further suggests that cells that did not express, or expressed lower levels of, CD105 proliferated at a faster rate than cells expressing CD105 and cells that did not, or expressed lower levels of, SSEA4 proliferated at a faster rate than cells expressing SSEA4.

These finding were consistent with the findings regarding unsorted donor populations from Donors 1, 2 and 3 presented above with respect to the correlation of CD105 negativity with proliferation rates. These findings were not fully consistent with respect to the correlation between SSEA-4 positivity and proliferation rates, perhaps due to factors such as donor variability, differences in culture conditions or the age of the cells. However, these findings did confirm that SSEA-4 positive and negative populations even from the same donor and having undergone equivalent expansion and culture conditions have different characteristics and thus may be useful for different applications.

The results presented here were unexpected in several respects. Both CD105 positivity and proliferation rate have been generally regarded as markers of cell "stemness" and potency. CD105 positivity has in fact been regarded as a necessary condition for designation of a cell as an MSC. CD105 positivity also correlated with c-kit positivity, which has been advanced as a marker for amniotic cell stemness and potency. Our data reflected to the contrary however that proliferation rate correlated negatively with CD105 positivity. Likewise, prior studies have suggested that amniotic cells are generally SSEA4 positive. However our data indicates that SSEA4 positive and negative populations are identifiable and have different characteristics even in cells from the same donor, and that SSEA 4 negative populations may proliferate more quickly than SSEA-4 positive populations under some conditions.

CONCLUSION

In conclusion, third trimester amniotic fluid derived cells are an easily obtainable and highly potent stem cell population. They are capable of rapidly proliferating and differentiating into multiple different lineages, one of which was confirmed in this study. Amniotic fluid cells isolated and cultured by the inventors were confirmed to have the characteristics of amniotic fluid derived stem cells from both the second and third trimester as assessed in various other studies (Roubelakis, Pappa et al. 2007; You, Cai et al. 2008; You, Tong et al. 2009; Zhang, Geng et al. 2010; Roubelakis, Trohatou et al. 2012). Furthermore, amniotic fluid cells demonstrated greater expansion rates and improved mineralization over time compared to adult bone marrow derived MSCs. Overall, the results highlight that these cells can serve as an attractive alternative to other currently available cellular therapies, and that individual populations can be isolated and expanded as described herein.

REFERENCES

Antonucci, I., I. Iezzi, et al. (2009). "Isolation of osteogenic progenitors from human amniotic fluid using a single step culture protocol." *BMC Biotechnol* 9: 9.
Arnhold, S., S. Gluer, et al. (2011). "Amniotic-Fluid Stem Cells: Growth Dynamics and Differentiation Potential after a CD-117-Based Selection Procedure." *Stem Cells Int* 2011: 715341.
Bai, J., Y. Wang, et al. (2012). "Human amniotic fluid-derived c-kit(+) and c-kit (−) stem cells: growth characteristics and some differentiation potential capacities comparison." *Cytotechnology* 64(5): 577-589.
Bernardo, M. E. and W. E. Fibbe (2012). "Safety and efficacy of mesenchymal stromal cell therapy in autoimmune disorders." *Ann N Y Acad Sci* 1266: 107-117.
Bobis, S., D. Jarocha, et al. (2006). "Mesenchymal stem cells: characteristics and clinical applications." *Folia Histochem Cytobiol* 44(4): 215-230.
Bottai, D., D. Cigognini, et al. (2012). "Third trimester amniotic fluid cells with the capacity to develop neural phenotypes and with heterogeneity among sub-populations." *Restor Neurol Neurosci* 30(1): 55-68.
Caplan, A. I. (1994). "The mesengenic process." *Clin Plast Surg* 21(3): 429-435.
De Coppi, P., G. Bartsch, Jr., et al. (2007). "Isolation of amniotic stem cell lines with potential for therapy." *Nat Biotechnol* 25(1): 100-106.
Delo, D. M., P. De Coppi, et al. (2006). "Amniotic fluid and placental stem cells." *Methods Enzymol* 419: 426-438.
Diaz-Prado S M, et al. *Cell Tissue Bank* 11, 183-195 (2010)
Dominici, M., Le Blanc, K., et al. (2006). "Minimal criteria for defining multipotent mesenchymal stromal cells. The International Society for Cellular Therapy position statement." *Cytotherapy* 8(4): 315-317.
Himes, P. (1999). "Early pregnancy prenatal diagnostic testing: risks associated with chorionic villus sampling and early amniocentesis and screening options." *J Perinat Neonatal Nurs* 13(2): 1-13.
In't Anker, P. S., S. A. Scherjon, et al. (2003). "Amniotic fluid as a novel source of mesenchymal stem cells for therapeutic transplantation." *Blood* 102(4): 1548-1549.
Jin C Z, et al. *Tiss Eng* 13, 693-702 (2007)
Kim, J., Y. Lee, et al. (2007). "Human amniotic fluid-derived stem cells have characteristics of multipotent stem cells." *Cell Prolif* 40(1): 75-90.
Liu, Y., L. Wang, et al. (2011). "Mesenchymal stem cell-based tissue regeneration is governed by recipient T lymphocytes via IFN-gamma and TNF-alpha." *Nat Med* 17(12): 1594-1601.
Marcus, A. J. and D. Woodbury (2008). "Fetal stem cells from extra-embryonic tissues: do not discard." *J Cell Mol Med* 12(3): 730-742.
Murphy, S. V. and A. Atala (2013). "Amniotic fluid and placental membranes: unexpected sources of highly multipotent cells." *Semin Reprod Med* 31(1): 62-68.
Okano, H., M. Nakamura, et al. (2013). "Steps toward safe cell therapy using induced pluripotent stem cells." *Circ Res* 112(3): 523-533.
Peister, A., M. A. Woodruff, et al. (2011). "Cell sourcing for bone tissue engineering: amniotic fluid stem cells have a delayed, robust differentiation compared to mesenchymal stem cells." *Stem Cell Res* 7(1): 17-27.
Pozzobon, M., Piccoli, M. et al. (2013). "Isolation of c-Kit+ human amniotic fluid stem cells from second trimester." *Methods Mol. Bio*. 1035:191-8.
Roelen, D. L., B. J. van der Mast, et al. (2009). "Differential immunomodulatory effects of fetal versus maternal multipotent stromal cells." *Hum Immunol* 70(1): 16-23.
Roubelakis, M. G., K. I. Pappa, et al. (2007). "Molecular and proteomic characterization of human mesenchymal stem cells derived from amniotic fluid: comparison to bone marrow mesenchymal stem cells." *Stem Cells Dev* 16(6): 931-952.
Roubelakis, M. G., 0. Trohatou, et al. (2012). "Amniotic fluid and amniotic membrane stem cells: marker discovery." *Stem Cells Int* 2012: 107836.
Tsai, M. S., J. L. Lee, et al. (2004). "Isolation of human multipotent mesenchymal stem cells from second-trimester amniotic fluid using a novel two-stage culture protocol." *Hum Reprod* 19(6): 1450-1456.
You, Q., L. Cai, et al. (2008). "Isolation of human mesenchymal stem cells from third-trimester amniotic fluid." *Int J Gynaecol Obstet* 103(2): 149-152.
You, Q., X. Tong, et al. (2009). "The biological characteristics of human third trimester amniotic fluid stem cells." *J Int Med Res* 37(1): 105-112.

Zaim, M., S. Karaman, et al. (2012). "Donor age and long-term culture affect differentiation and proliferation of human bone marrow mesenchymal stem cells." *Ann Hematol* 91(8): 1175-1186.

Zhang, S., H. Geng, et al. (2010). "The heterogeneity of cell subtypes from a primary culture of human amniotic fluid." *Cell Mol Biol Lett* 15(3): 424-439.

Zhou, S., J. S. Greenberger, et al. (2008). "Age-related intrinsic changes in human bone-marrow-derived mesenchymal stem cells and their differentiation to osteoblasts." *Aging Cell* 7(3): 335-343.

Now, therefore, the following is claimed:

1. A method of harvesting human prenatal stem cells comprising:
   providing a human prenatal sample;
   collecting cells from the sample;
   selecting CD105 negative cells from the sample, and
   selecting from the CD 105 negative cells, cells that are CD44 positive, CD90 positive or both CD44 positive and CD90 positive thereby obtaining CD105 negative cells that are CD44 positive, CD90 positive or both CD44 positive and CD90 positive.

2. The method of claim 1, wherein the prenatal sample comprises prenatal fluid.

3. The method of claim 2, wherein the prenatal fluid comprises third trimester amniotic fluid.

4. The method of claim 1, wherein the prenatal sample comprises prenatal membrane.

5. The method of claim 4, wherein the prenatal membrane comprises placental membrane.

6. The method of claim 1, wherein the selecting of the CD105 negative cells comprises the steps of:
   incubating a plurality of cells from the human prenatal sample with a first antibody reactive to CD105; and
   selecting from the plurality of cells a group of cells that are not reactive with the first antibody.

7. The method of claim 6, wherein the selecting from the plurality of cells a group of cells that are not reactive with the first antibody is accomplished by an immunoselection technique.

8. The method of claim 7, where the immunoselection technique is selected from the group consisting of flow cytometry, activated cells sorting and immune-magnetic selection.

9. The method of claim 1, further comprising selecting c-kit negative cells from the CD105 negative cells.

10. A method of harvesting human prenatal stem cells comprising:
    providing a human prenatal sample;
    collecting cells from the sample;
    selecting CD105 negative cells from the sample, wherein the CD105 negative cells are CD44 positive or both CD44 positive and CD90 positive, wherein the selecting of the CD105 negative cells comprises the steps of:
       incubating a plurality of cells from the human prenatal sample with a first antibody reactive to CD105; and
       selecting from the plurality of cells a group of cells that are not reactive with the first antibody
    incubating the group of cells that are not reactive with the first antibody with a second antibody that is reactive to CD44; and
    selecting from the group of cells that are not reactive with the first antibody a second group of cell that are reactive with the second antibody.

11. A method of proliferating a population of human prenatal stem cells comprising:
    providing a human prenatal sample including CD105 negative cells and CD105 positive cells;
    isolating the CD105 negative cells from the CD105 positive cells, the isolated CD105 negative cells having a greater proliferation rate than the isolated CD105 positive cells;
    selecting from the isolated CD 105 negative cells, cells that are CD44 positive, CD90 positive or both CD44 positive and CD90 positive thereby obtaining CD105 negative cells that are CD44 positive, CD90 positive or both CD44 positive and CD90 positive; and thereafter,
    proliferating the CD105 negative cells that are CD44 positive, CD90 positive or both CD44 positive and CD90 positive.

12. A method of proliferating a population of human prenatal stem cells comprising:
    providing a human prenatal sample including CD105 negative cells and CD105 positive cells;
    isolating the CD105 negative cells from the CD105 positive cells, the isolated CD105 negative cells having a greater proliferation rate than the isolated CD105 positive cells and wherein the isolated CD105 negative cells include SSEA4 negative cells and SSEA4 positive cells;
    proliferating the isolated CD105 negative cells;
    isolating from the isolated CD105 negative cells the SSEA4 negative cells; and
    proliferating the SSEA4 negative cells, the SSEA4 negative cells having a greater proliferation rate than the SSEA4 positive cells.

* * * * *